US012662447B2

(12) United States Patent
Nishio et al.

(10) Patent No.: US 12,662,447 B2
(45) **Date of Patent: *Jun. 23, 2026**

(54) METHOD OF PRODUCING CARBONYL COMPOUND AND FLOW TYPE REACTION SYSTEM OF PRODUCING CARBONYL COMPOUND

(71) Applicant: FUJIFILM Corporation, Tokyo (JP)

(72) Inventors: Ryo Nishio, Kanagawa (JP); Kenji Wada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 858 days.

This patent is subject to a terminal disclaimer.

(21) Appl. No.: 17/580,657

(22) Filed: Jan. 21, 2022

(65) Prior Publication Data

US 2022/0144760 A1 May 12, 2022

Related U.S. Application Data

(63) Continuation of application No. PCT/JP2020/028914, filed on Jul. 28, 2020.

(30) Foreign Application Priority Data

Aug. 22, 2019 (JP) ................................ 2019-152112

(51) Int. Cl.
*C07C 263/10* (2006.01)
*B01J 19/18* (2006.01)
(Continued)

(52) U.S. Cl.
CPC ......... *C07C 263/10* (2013.01); *B01J 19/1831* (2013.01); *B01J 31/06* (2013.01);
(Continued)

(58) Field of Classification Search
None
See application file for complete search history.

(56) References Cited

U.S. PATENT DOCUMENTS 6,399,822 B1 6/2002 Eckert et al.
9,175,135 B2 11/2015 Ooms et al.
(Continued)

FOREIGN PATENT DOCUMENTS

CN 1275962 12/2000
CN 107324334 11/2017
(Continued)

OTHER PUBLICATIONS

Machine generated English language translation of Xue (CN107324334A, published on Nov. 7, 2017), obtained on Dec. 17, 2024 (Year: 2024).*
(Continued)

*Primary Examiner* — Amy C Bonaparte
(74) *Attorney, Agent, or Firm* — JCIPRNET

(57) ABSTRACT

There are provided a method of producing a carbonyl compound by a flow type reaction, including introducing a triphosgene solution into a flow channel (I), bringing the triphosgene solution into contact with a solid catalyst immobilized in at least a part of the flow channel (I) to generate a phosgene solution while the triphosgene solution is flowing through the flow channel (I), joining the phosgene solution and an active hydrogen-containing compound solution that flows inside the flow channel (II), which are subsequently allowed to flow downstream inside a reaction flow channel to be reacted in a presence of a tertiary amine, and obtaining a carbonyl compound in a joining solution; and a flow type reaction system that is suitable for carrying out this production method.

11 Claims, 2 Drawing Sheets

(51) Int. Cl.
*B01J 31/06* (2006.01)
*B01J 19/00* (2006.01)
*B01J 19/24* (2006.01)

(52) U.S. Cl.
CPC .......... *B01J 19/0093* (2013.01); *B01J 19/248* (2013.01); *B01J 2219/2401* (2013.01); *B01J 2219/243* (2013.01)

(56) References Cited

U.S. PATENT DOCUMENTS

| | | | | |
|---|---|---|---|---|
| 11,161,820 | B2 | 11/2021 | Yasukouchi et al. | |
| 2019/0144404 | A1 | 5/2019 | Yasukouchi et al. | |
| 2019/0177262 | A1 | 6/2019 | Yasukouchi et al. | |
| 2020/0207717 | A1* | 7/2020 | Yasukouchi | C01B 32/80 |

FOREIGN PATENT DOCUMENTS

| | | |
|---|---|---|
| CN | 109563020 | 4/2019 |
| JP | 2001516692 | 10/2001 |
| JP | 2011006367 | 1/2011 |
| JP | 2011207883 | 10/2011 |
| WO | 2018016376 | 1/2018 |
| WO | 2018016377 | 1/2018 |
| WO | 2019049584 | 3/2019 |

OTHER PUBLICATIONS

"Office Action of China Counterpart Application", issued on Apr. 19, 2024, with English translation thereof, p. 1-p. 20.

Shinichiro Fuse et al., "Continuous in situ generation and reaction of phosgene in a microflow system," Chemical Communications, Nov. 2011, pp. 1-12.

"International Search Report (Form PCT/ISA/210) of PCT/JP2020/028914," mailed on Sep. 15, 2020, with English translation thereof, pp. 1-7.

"Written Opinion of the International Searching Authority (Form PCT/ISA/237)" of PCT/JP2020/028914, mailed on Sep. 15, 2020, with English translation thereof, pp. 1-8.

Office Action of Japan Counterpart Application, with English translation thereof, issued on Aug. 23, 2022, pp. 1-6.

"Office Action of China Counterpart Application", issued on Jan. 3, 2024, with English translation thereof, p. 1-p. 13.

"Search Report of Europe Counterpart Application", issued on Sep. 14, 2022, p. 1-p. 6.

* cited by examiner

METHOD OF PRODUCING CARBONYL COMPOUND AND FLOW TYPE REACTION SYSTEM OF PRODUCING CARBONYL COMPOUND

CROSS-REFERENCE TO RELATED APPLICATIONS

This application is a Continuation of PCT International Application No. PCT/JP2020/028914 filed on Jul. 28, 2020, which claims priority under 35 U.S.C. § 119 (a) to Japanese Patent Application No. 2019-152112 filed in Japan on Aug. 22, 2019. Each of the above applications is hereby expressly incorporated by reference, in its entirety, into the present application.

BACKGROUND OF THE INVENTION

1. Field of the Invention

The present invention relates to a method of producing a carbonyl compound. In addition, the present invention relates to a flow type reaction system of producing a carbonyl compound.

2. Description of the Related Art

Phosgene is known as a reactant for introducing a carbonyl group into various compounds containing active hydrogen. For example, an isocyanate compound, a urea compound, or the like can be obtained by a reaction with a primary amine, and a carbonate compound, a chloroformate compound, or the like can be obtained by a reaction with a compound having a hydroxyl group (see, for example, WO2018/016377A, JP2011-207883A, and JP2011-006367A).

Since phosgene is extremely toxic and gaseous at room temperature, it should be handled with great care. On the other hand, triphosgene is known as a compound equivalent to the phosgene trimer. Triphosgene is solid at room temperature and is relatively safe.

In a reaction in which triphosgene is used, three molecules of phosgene are generated from triphosgene by using a tertiary amine or the like as a catalyst, and this phosgene is reacted with a reaction substrate to obtain a target carbonyl compound. As a result, even in a case where triphosgene is used, conversion to phosgene is indispensable, and safety measures such as sealing of the reaction system are required.

As a technique for dealing with this problem, WO2018/016377A describes applying a flow reactor to the above reaction. In this technique, a solution containing triphosgene and a solution containing a tertiary amine such as tributylamine and an alcohol compound are mixed and reacted in a virtually closed space called a flow reactor. According to WO2018/016377A, it is said that in a case where triphosgene is brought into contact with a tertiary amine to generate phosgene by such a reaction form, the phosgene is rapidly consumed by the alcohol compound, and as a result, it is possible to stably prevent the increase in the concentration of the highly toxic phosgene in the reaction solution.

It is noted that the tertiary amine, which acts as a catalyst for converting triphosgene into phosgene, also acts as a base for neutralizing hydrochloric acid that is generated in the reaction solution.

SUMMARY OF THE INVENTION

According to the technique described in WO2018/016377A, it is said that phosgene is generated in a closed space by using triphosgene, which is safer than phosgene, and a generated phosgene and an alcohol compound can be continuously reacted with high efficiency.

However, as a result of studies carried out by the inventors of the present invention, it was found that in the flow type reaction described in WO2018/016377A, the efficiency of converting triphosgene into phosgene is not sufficient, where the conversion is catalyzed by a tertiary amine, and that in a case where this conversion efficiency is not sufficient, impurities tend to increase, which limits the improvement of the purity of the target carbonyl compound to be obtained.

An object of the present invention is to provide a method of producing a carbonyl-compound, which makes it possible to obtain a target carbonyl compound safely, continuously, and with high purity by using triphosgene and an active hydrogen-containing compound as starting materials. In addition, another object of the present invention is to provide a flow type reaction system suitable for carrying out the above production method.

As a result of extensive studies in consideration of the above problems, the inventors of the present invention have found that the efficiency of converting triphosgene into phosgene can be dramatically increased and the above problems can be solved by adopting a configuration in which a catalyst for converting triphosgene to three molecules of phosgene is immobilized in the flow channel through which a triphosgene solution flows and phosgene is generated while a triphosgene solution flows inside the flow channel. Based on these findings, further studies were repeated, and as a result, the present invention has been completed.

That is, the objects of the present invention have been achieved by the following means.

[1] A Method of producing a carbonyl compound by a flow type reaction, comprising:

introducing a triphosgene solution into a flow channel (I), bringing the triphosgene solution into contact with a solid catalyst immobilized in at least a part of the flow channel (I) to generate a phosgene solution while the triphosgene solution is flowing through the flow channel (I), joining the phosgene solution and an active hydrogen-containing compound solution that flows inside a flow channel (II), which are subsequently allowed to flow downstream inside a reaction flow channel to be reacted in a presence of a tertiary amine, and obtaining a carbonyl compound in the joining solution.

[2] The method of producing a carbonyl compound according to [1], in which a temperature in the reaction flow channel is set to be lower than a boiling point of a solvent of which the boiling point is lowest among solvents that are used in the reaction.

[3] The method of producing a carbonyl compound according to [1] or [2], in which a column filled with the solid catalyst is incorporated in the flow channel (I) to immobilize the solid catalyst in the flow channel (I).

[4] The method of producing a carbonyl compound according to any one of [1] to [3], in which the solid catalyst is insoluble in a solvent in the triphosgene solution.

[5] The method of producing a carbonyl compound according to any one of [1] to [4], in which the solid catalyst is a polymer.

[6] The method of producing a carbonyl compound according to [5], in which the polymer has a heteroatom.

[7] The method of producing a carbonyl compound according to any one of [1] to [6], in which the tertiary amine has a cyclic structure.

[8] The method of producing a carbonyl compound according to any one of [1] to [7], in which the tertiary amine has 6 to 40 carbon atoms.

[9] The method of producing a carbonyl compound according to any one of [1] to [8], in which the active hydrogen-containing compound is at least one of a primary amine, a secondary amine, an alcohol, a thiol, a carboxylic acid, or an amino acid.

[10] The method of producing a carbonyl compound according to any one of [1] to [9], in which the active hydrogen-containing compound is a primary amine.

[11] The method of producing a carbonyl compound according to any one of [1] to [10], in which a dehydrating agent is arranged in at least a part of the flow channel that is used in the flow type reaction.

[12] A flow type reaction system of producing a carbonyl compound, comprising at least:

a first flow channel into which a triphosgene solution is introduced; a second flow channel into which an active hydrogen-containing compound solution is introduced; a joining part at which the first flow channel and the second flow channel are joined; and a reaction pipe which is connected downstream of the joining part, in which a solid catalyst that converts triphosgene into phosgene is immobilized in at least a part of the first flow channel.

[13] The flow type reaction system according to [12], in which a third flow channel into which a tertiary amine solution is introduced is joined at the joining part or upstream of the joining part.

In the present specification, numerical ranges expressed using "to" include numerical values before and after the "to" as the lower limit value and the upper limit value.

In a case where an intra-pipe cross-sectional size (an equivalent diameter) of a flow channel, a joining part, a mixer, or the like is described in the present specification, the above size refers to a size excluding a connecting portion between flow channels, a connecting portion between a flow channel and a joining part, or a connecting portion between a flow channel and a mixer. That is, the size of each of the above connecting portions is appropriately adjusted by using a connecting tube or the like so that a fluid flows through the connecting portion from the upstream to the downstream.

According to the method of producing a carbonyl compound according to an aspect of the present invention, a target carbonyl compound can be obtained safely, continuously, and with high purity. Further, in the flow type reaction system according to an aspect of the present invention, a target carbonyl compound can be obtained safely, continuously, and with high purity by carrying out the above-described production method using the flow type reaction system.

DESCRIPTION OF THE PREFERRED EMBODIMENTS

Figure 1:
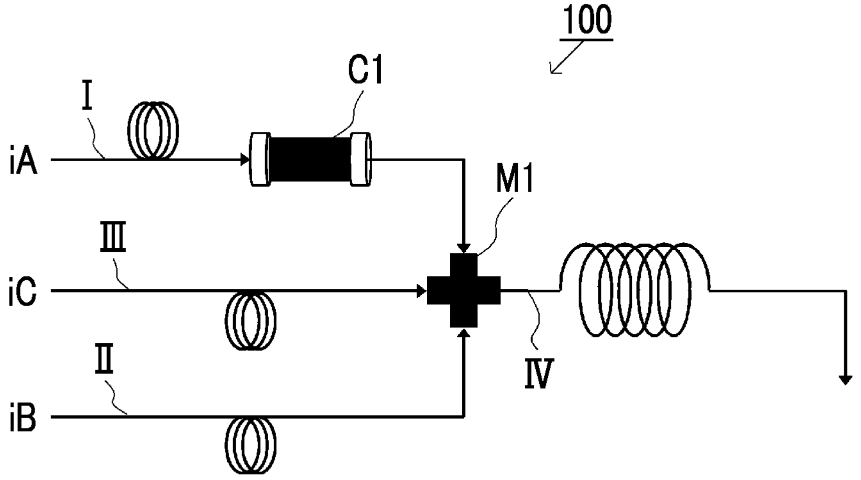
FIG. 1 is an illustrative view illustrating an outline of one embodiment of a flow type reaction system according to the embodiment of the present invention.

[Production of Carbonyl Compound by Flow Type Reaction]

In a method of producing a carbonyl compound according to the embodiment of the present invention (hereinafter, also referred to as a "production method according to the embodiment of the present invention"), a flow type reaction is adopted. In this flow type reaction, a triphosgene solution obtained by dissolving triphosgene in a solvent is introduced into one flow channel (I) and allowed to flow inside the flow channel (I). A solid catalyst that converts triphosgene into phosgene is immobilized in at least a part of the flow channel (I) (a part or the whole of the flow channel (I)). As a result, the triphosgene solution is brought into contact with the solid catalyst while flowing inside the flow channel (I), whereby phosgene is generated. That is, a phosgene solution is generated.

In the present invention, the description the solid catalyst is "immobilized" in the flow channel means that the solid catalyst remains in the initially arranged flow channel even in a case where the triphosgene solution flows. There is no particular limitation on the configuration of this immobilization. Examples of the configuration thereof include a configuration in which a solid catalyst is immobilized on the wall surface of the flow channel. Further, a configuration in which a solid catalyst is filled in a column and this column is incorporated in the flow channel (I) (a configuration in which the column is provided as a part of the flow channel (I)) is also preferable. In addition, a configuration in which the flow channel (I) is directly filled with a solid catalyst can be adopted. The solid catalyst is preferably insoluble in the solvent of the triphosgene solution with which the solid catalyst is brought into contact.

Further, the solid catalyst may be discontinuously immobilized in the flow channel (I). That is, the solid catalyst may be intermittently immobilized in a plurality of regions in the flow channel (I) in the length direction of the flow channel (I).

On the other hand, an active hydrogen-containing compound solution obtained by dissolving in a solvent an active hydrogen-containing compound, which is a reaction substrate that reacts with phosgene, is introduced into a flow channel (II) different from the flow channel (I) and allowed to flows in the flow channel (II). In the present invention, the "active hydrogen" means a hydrogen atom bonded to a nitrogen atom, an oxygen atom, or a sulfur atom.

The flow channel (I) and the flow channel (II) are joined on the side opposite to the solution introduction port, whereby the phosgene solution (a phosgene solution generated by converting triphosgene of the triphosgene solution into phosgene by the action of the solid catalyst) that flows inside the flow channel (I) and the active hydrogen-containing compound solution that flows inside the flow channel (II) are joined and flows downstream inside the reaction flow channel. A reaction (a flow reaction) between phosgene and an active hydrogen-containing compound occurs in this joining solution to generate a target carbonyl compound.

Hydrochloric acid is generated in the reaction in the joining solution, and thus it is necessary to be neutralized. For this reason, in the present invention, the flow reaction is carried out in the presence of a tertiary amine. The tertiary amine form an ammonium salt with hydrochloric acid.

A configuration in which this tertiary amine is added at the joining part between the flow channel (I) and the flow channel (II) can be adopted. In addition, it is also preferable to adopt a configuration in which the tertiary amine is added into the flow channel (I) before the flow channel (I) and the flow channel (II) are joined. In the configuration in which the tertiary amine is added into the flow channel (I), it may be joined upstream of the solid catalyst or may be joined downstream of the solid catalyst. It is preferably joined downstream of the solid catalyst. It is preferable that this tertiary amine is dissolved in a solvent and added in a state of a tertiary amine solution.

Further, the tertiary amine can also be dissolved in an active hydrogen-containing compound solution and allowed to flow inside the flow channel (II).

In any one of the above configurations, the reaction of phosgene with the active hydrogen-containing compound can be carried out in the presence of a tertiary amine.

In the present specification, the terms "upstream" and "downstream" are used with respect to the direction in which a liquid flows, and a side where a liquid is introduced (a side where a liquid flows in) is upstream, and a side where a liquid flows out is downstream.

In the flow type reaction according to the embodiment of the present invention, it is preferable that the temperature in the reaction flow channel is set to be at least lower than a boiling point of a solvent of which the boiling point is lowest among solvents that are used in the reaction. This makes it possible to carry out the reaction more reliably in the liquid phase state. It is noted that in a case where one kind of solvent is used, the above-described "lower than a boiling point of a solvent of which the boiling point is lowest" is lower than the boiling point of this one kind of solvent.

One embodiment of the flow type reaction system that is used in the present invention will be described with reference to the drawings. It is be noted that each drawing is an illustrative view for facilitating the understanding of the present invention, and the magnitude of the size, the relative magnitude relationship, or the like of each member may be changed for the convenience of description, and it does not indicate the actual magnitude relationship as it is. Further, matters other than those specified in the present invention are not limited to the outer shape and the shape illustrated in these drawings.

FIG. 1 is a schematic view illustrating an example of a flow type reaction system that is used in the production method according to the embodiment of the present invention. A flow type reaction system (100) illustrated in FIG. 1 has a flow channel (I) having an introduction port (iA) into which a triphosgene solution is introduced, a flow channel (II) having an introduction port (iB) into which an active hydrogen-containing compound solution is introduced, a joining part (M1) at which the flow channel (I) and the flow channel (II) are joined, and a reaction pipe (IV) that is connected to the downstream end portion of the joining part (M1). The flow type reaction system of FIG. 1 has a flow channel (III) having an introduction port (iC) into which a tertiary amine solution is introduced, and the flow channel (III) is also joined at the joining part (M1).

In addition, a column (C1) filled with a solid catalyst is arranged in the middle of the flow channel (I), and this column (C1) constitutes a part of the flow channel (I), and a triphosgene solution flows inside the column (C1).

Liquid feeding pumps (not illustrated in the drawing) such as syringe pumps are usually connected to the introduction ports (iA), (iB), and (iC), respectively, and in a case where these pumps are operated, it is possible to adopt a configuration in which a triphosgene solution, an active hydrogen-containing compound solution, a tertiary amine solution flow inside flow channels, respectively, at a desired flow speed.

Each configuration of the embodiment illustrated in FIG. 1 will be described in more detail.

<Flow Channel (I)>

The flow channel (I) is a flow channel in which a triphosgene solution introduced from the introduction port (iA) is converted into a phosgene solution by a solid catalyst, which is immobilized in the flow channel (I), and supplied to the joining part (M1). The following description for the flow channel (I) is a description for the portion excluding the column (C1) unless otherwise specified.

The flow channel (I) is preferably set to have an equivalent diameter of 0.2 to 50 mm. In a case where the equivalent diameter of the flow channel (I) is set to 0.2 mm or more, it is possible to suppress an increase in pressure during liquid feeding, and it is possible to suppress the clogging of the flow channel even in a case where an insoluble matter is generated. In addition, in a case where the equivalent diameter of the flow channel (I) is set to 50 mm or less, it is possible to suitably control the liquid temperature at the time of being introduced into the joining part (M1). The equivalent diameter of the flow channel (I) is more preferably 0.5 to 30 mm and still more preferably 1 to 20 mm.

The "equivalent diameter" is a term used in the field of mechanical engineering. In a case of assuming a circular pipe that is equivalent to a pipe or flow channel having any intra-pipe cross-sectional shape, a diameter of the intra-pipe cross-section of the equivalent circular pipe is referred to as the equivalent diameter. The equivalent diameter (deq) is defined by using A: an intra-pipe cross-sectional area of a pipe, and p: a wetted perimeter (inner circumference) of the pipe, as deq=4A/p. In a case of being applied to a circular pipe, this equivalent diameter corresponds to the diameter of the intra-pipe cross section of the circular pipe. The equivalent diameter is used to estimate the flow or the heat transfer characteristics of a pipe based on the data of the equivalent circular pipe and represents the spatial scale (the representative length) of the phenomenon. In a case of a square pipe in which the intra-pipe cross section has a side of a, the equivalent diameter is $deq=4a^2/4a=a$, in a case of an equilateral triangle pipe in which the intra-pipe cross section has a side of a, the equivalent diameter is $deq=a/3^{1/2}$, and in a case of a flow between flat plates parallel to the flow channel having a height of h, the equivalent diameter is deq=2 h (see, for example, "Mechanical Engineering Dictionary" edited by The Japan Society of Mechanical Engineers, 1997, Maruzen Publishing Co., Ltd.).

The length of the flow channel (I) is not particularly limited, and for example, it can be constituted of a tube having a length of about 10 cm to 15 m (preferably 30 cm to 10 m).

The material of the tube is not particularly limited, and examples thereof include a perfluoroalkoxy alkane (PFA), Teflon (registered trade name), an aromatic polyether ketone-based resin, stainless steel, copper or a copper alloy, nickel or a nickel alloy, titanium or a titanium alloy, quartz glass, and lime soda glass. From the viewpoint of flexibility and chemical resistance, the material of the tube is preferably PFA, Teflon (registered trade name), stainless steel, a nickel alloy, or titanium is preferable.

The flow speed for introducing the triphosgene solution from the introduction port (iA) is not particularly limited, and it can be appropriately set depending on the intended purpose in consideration of the equivalent diameter of the flow channel, the concentration of the triphosgene solution, the concentration of the active hydrogen-containing compound solution, the introduction flow rate of the active hydrogen-containing compound solution, and the like. For example, 0.1 to 5,000 mL/minutes (min) is preferable, 0.5 to 3,000 mL/min is more preferable, and 1 to 3,000 mL/min is still more preferable.

—Triphosgene Solution—

The triphosgene solution that is introduced into the flow channel (I) is a solution obtained by dissolving triphosgene in a solvent. The solvent contained in the triphosgene solution is usually an organic solvent. Examples of this organic solvent include a halogen-containing solvent, an ether solvent having a linear, branched, or cyclic structure, and a hydrocarbon solvent.

Examples of the halogen-containing solvent include methylene chloride, chloroform, dichloroethane, carbon tetrachloride, chlorobenzene, and o-dichlorobenzene.

Examples of the ether solvent include tetrahydrofuran, dioxane, methyl tertiary butyl ether, cyclopentyl methyl ether, ethylene glycol dibutyl ether, diethylene glycol dimethyl ether, diethylene glycol diethyl ether, diethylene glycol dibutyl ether, and derivatives thereof.

Examples of the hydrocarbon solvent include hexane, heptane, octane, cyclohexane, methyl cyclohexane, benzene, toluene, xylene, mesitylene, decalin, tetralin, and derivatives thereof.

In addition, the following can be used as the above organic solvent; a ketone-based solvent such as acetone, methyl ethyl ketone, diisobutyl ketone, cyclohexanone, or methyl isobutyl ketone, a nitrile-based solvent such as acetonitrile, a lactone-based solvent such as γ-butyrolactone, an ester-based solvent such as ethyl acetate or butyl acetate, and an amide-based solvent such as dimethyl acetamide or dimethyl formamide.

The above solvent may be used alone, or two or more kinds thereof may be used in a state of being mixed.

Among them, at least one of methylene chloride, chloroform, chlorobenzene, o-dichlorobenzene, tetrahydrofuran, dioxane, toluene, xylene, mesitylene, cyclohexanone, methyl ethyl ketone, or acetonitrile is preferably used, at least one of methylene chloride, chlorobenzene, o-dichlorobenzene, tetrahydrofuran, toluene, xylene, mesitylene, or acetonitrile is more preferably used, and at least one of methylene chloride, toluene, mesitylene, chlorobenzene, or acetonitrile is still more preferably used.

The content of triphosgene in the triphosgene solution is not particularly limited, and it is appropriately adjusted in consideration of the introduction flow rate of the triphosgene solution, the concentration of the active hydrogen-containing compound solution, the introduction flow rate of the active hydrogen-containing compound solution, and the like. The content of triphosgene in the triphosgene solution can be, for example, 0.01 to 10 M (mol/liter), and it is preferably 0.03 to 3 M and more preferably 0.05 to 1 M.

—Solid Catalyst—

In FIG. 1, the column (C1) filled with a solid catalyst is incorporated in the middle of the flow channel (I), whereby the solid catalyst is immobilized in a part of the flow channel (I). The solid catalyst will be described below; however, the description for this solid catalyst applies not only to the configuration in which the column of FIG. 1 is filled with the solid catalyst but also to the solid catalyst in all the embodiments included in the present invention.

The solid catalyst is a conversion catalyst that acts on triphosgene to generate three molecules of phosgene. This solid catalyst is preferably insoluble in a solvent with which the solid catalyst is brought into contact. Examples of the method of insolubilizing a solid catalyst include using polymerization, introduction of a crosslinked structure, microencapsulation, core shelling, inclusion, complexation, introduction of an intramolecular or intermolecular electrostatic interaction or a hydrogen bond, or a material poorly compatible with a solvent.

Examples of the solid catalyst that can be used in the present invention include a polymer, activated carbon, an ion exchange resin, a metal complex supported on a polymer, a metal complex crosslinked by a polymer, and a charge transfer complex. The solid catalyst preferably does not have active hydrogen.

Examples of the polymer suitable as the solid catalyst include crosslinked heterocyclic ring-containing polymers such as a crosslinked polyvinylpyridine and a crosslinked polyvinylcarbazole; heteroatom-containing conjugated polymers such as polyaniline and polythiophene; polymers having an amide group in the side chain, such as poly-N-isopropyl acrylamide; and polymers having an alkylamino group in the side chain, such as dimethylaminoethyl methacrylate. The polymer that is used as a solid catalyst preferably has at least one heteroatom (for example, a nitrogen atom, a sulfur atom, an oxygen atom, or the like), more preferably has a heterocyclic ring, and still more preferably has a nitrogen-containing heterocyclic ring having a nitrogen atom as the ring-constituting atom. That is, at least one constitutional component that constitutes a polymer preferably has a heteroatom, more preferably has a heterocyclic ring, and still more preferably a nitrogen-containing heterocyclic ring.

The introduction of the crosslinked structure into the polymer (for example, the formation of the crosslinked structure in the crosslinked heterocyclic ring-containing polymer) can be carried out by a general method. For example, it can be carried out by copolymerizing with a polyfunctional monomer such as divinylbenzene, ethylene glycol dimethacrylate, or dipentaerythritol hexaacrylate. The copolymerization ratio is appropriately set depending on the intended purpose. Further, it is possible to form a crosslinked structure by reacting a reactive active group such as an amino group, a hydroxyl group, or a thiol group in a polymer with a crosslinking agent such as a polyfunctional isocyanate compound, a polyfunctional epoxy compound, a polyfunctional olefin, or a polyfunctional carboxylic acid.

The solid catalyst is preferably at least one of a crosslinked heterocyclic ring-containing polymer, activated carbon, or an imidazole group-modified polymer is preferable, and crosslinked polyvinylpyridine is more preferable. The crosslinked polyvinylpyridine is preferably a copolymer of vinylpyridine and divinylbenzene.

In the present invention, one kind of solid catalyst may be used as the solid catalyst, or two or more kinds thereof may be used in combination.

In FIG. 1, a solid catalyst is filled in a column, and this column (C1) is incorporated in the middle of the flow channel (I). The equivalent diameter of the column (C1) is not particularly limited. It is generally larger than the equivalent diameter of the portion of the flow channel (I) other than the column (C1) although it depends on the equivalent diameter of the flow channel (I). For example, the equivalent diameter of the column can be made to be 1.5 to 60 times and can also be made to be about 2 to 30 times the equivalent diameter of the portion of the flow channel (I) other than the column.

In addition, the material of the column (the material of the column container) is not particularly limited, and it is appropriately set depending on the intended purpose. For example, a column of which the material is stainless steel, HASTELLOY, a titanium alloy, glass lining, polytetrafluoroethylene (PTFE), perfluoroalkoxy alkane (PFA), or the like can be filled with a solid catalyst and applied to the present invention.

The temperature of the flow channel (I) is preferably set to be lower than the boiling point of the solvent used to prepare the triphosgene solution. For example, it can be set to −60° C. to 80° C., and it is preferably −20° C. to 30° C. and still more preferably −10° C. to 20° C.

<Flow Channel (II)>

The flow channel (II) is a flow channel in which the active hydrogen-containing compound solution introduced from the introduction port (iB) is supplied to the joining part (M1). The flow channel (II) is preferably set to have an equivalent diameter of 0.1 to 50 mm. In a case where the equivalent diameter of the flow channel (II) is set to 0.1 mm or more, it is possible to suppress an increase in pressure during liquid feeding, and it is possible to suppress the clogging of the flow channel even in a case where an insoluble matter is generated. In addition, in a case where the equivalent diameter of the flow channel (II) is set to 50 mm or less, it is possible to suitably control the liquid temperature at the time of being introduced into joining part (M1). The equivalent diameter of the flow channel (II) is more preferably 0.5 to 30 mm and still more preferably 1 to 20 mm.

The length of the flow channel (II) is not particularly limited, and for example, it can be constituted of a tube having a length of about 10 cm to 15 m (preferably 30 cm to 10 m).

The material of the tube is not particularly limited, and the tube of the material exemplified in the above flow channel (I) can be used.

The flow speed for introducing the active hydrogen-containing compound solution from the introduction port (iB) is not particularly limited, and it can be appropriately set depending on the intended purpose in consideration of the equivalent diameter of the flow channel, the concentration of the triphosgene solution, the concentration of the active hydrogen-containing compound solution, the introduction flow rate of the triphosgene solution, and the like. For example, 0.1 to 5,000 mL/minutes (min) is preferable, 0.5 to 3,000 mL/min is more preferable, and 1 to 3,000 mL/min is still more preferable.

In addition, the relationship between the flow speed rB for introducing the active hydrogen-containing compound solution from the introduction port (iB) and the flow speed rA for introducing the triphosgene solution from the introduction port (iA) is not particularly limited, and the flow speeds therefor can be appropriately set in consideration of the concentrations of the respective solutions. For example, the relationship therebetween can be set to [flow speed rA]/[flow speed rB]=10/1 to 1/10, and it is preferably [flow speed rA]/[flow speed rB]=5/1 to 1/5. It is noted that in the present specification, the unit of the flow speed is mL/min.

—Active Hydrogen-Containing Compound Solution—

The active hydrogen-containing compound solution that is allowed to flow inside the flow channel (II) is generally a solution obtained by dissolving an active hydrogen-containing compound in a solvent. The solvent contained in the active hydrogen-containing compound solution is usually an organic solvent. As the organic solvent, those exemplified as the solvent of the above-described triphosgene solution can be preferably used. The active hydrogen-containing compound solution and the triphosgene solution may use the same solvent, or the kinds of solvents thereof may be different from each other. In a case where the kinds of solvents thereof are different from each other, it is preferable to use solvents that are compatible with each other (solvents that do not phase-separate in a case of being mixed).

(Active Hydrogen-Containing Compound)

An active hydrogen-containing compound in the active hydrogen-containing compound solution is not particularly limited, and for example, a compound having at least one group selected from —OH, —COOH, $—NH_2$, —NHR (R is a substituent), or —SH can be widely used. The active hydrogen-containing compound is, for example, at least one of a primary amine, a secondary amine, an alcohol, a thiol, a carboxylic acid, or an amino acid.

The reaction itself for introducing a carbonyl group by reacting this active hydrogen-containing group with phosgene is known, and the reaction conditions and the like are appropriately set depending on the target reaction. An isocyanate compound, a carbamoyl chloride compound, a urea compound, or the like can be obtained by reacting a compound having $—NH_2$ with phosgene as an example of the above reaction. In addition, a carbonate compound, a chloroformate compound, or the like can be obtained by reacting a compound having —OH with phosgene. In addition, an acid chloride compound can be obtained by reacting a compound having —COOH with phosgene. Further, an amino acid anhydride can be obtained by reacting an amino acid with phosgene.

Among the above, the active hydrogen-containing compound is preferably a primary amine, a secondary amine, an alcohol, or an amino acid, and it is more preferably a primary amine.

The active hydrogen-containing compound, which is a reaction substrate, preferably has a molecular weight of 40 to 1,000 and more preferably 60 to 500.

The content of the active hydrogen-containing compound in the active hydrogen-containing compound solution is not particularly limited, and it is appropriately adjusted in consideration of the introduction flow rate of the active hydrogen-containing compound solution, the concentration of the triphosgene solution, the introduction flow rate of the triphosgene solution, and the like. The content of the active hydrogen-containing compound in the active hydrogen-containing compound solution can be set to, for example, 0.02 to 10 M (mol/liter) and it is preferably 0.05 to 3 M and more preferably 0.07 to 1 M.

The temperature of the flow channel (II) is preferably set to be lower than the boiling point of the solvent used to prepare the active hydrogen-containing compound solution. For example, it can be set to −60° C. to 80° C., and it is preferably −20° C. to 30° C. and still more preferably −10° C. to 20° C.

<Joining Part (M1)>

The triphosgene solution introduced into the flow channel (I) passes through the column (C1) to become a phosgene solution and is joined with the active hydrogen-containing compound solution that flows inside the flow channel (II), at the joining part (M1). The joining part (M1) is not particularly limited as long as it has a role of a mixer, can join the flow channel (I) and the flow channel (II) into one flow channel, and can send the joined solution to the reaction pipe (IV) that is connected to the downstream end portion of the joining part (M1).

In the embodiment of FIG. 1, a cross-shaped connector having four connection ports is used as the joining part (M1). In this cross-shaped connector, the flow channel (III) is connected to a connection port other than the three connection ports that are connected to the flow channel (I), the flow channel (II), and the reaction pipe (IV), and a tertiary amine solution is allowed to flow inside this flow channel (III). This makes it possible to carry out the reaction between phosgene and the active hydrogen-containing compound in the presence of a tertiary amine (a neutralizing agent which is non-reactive to phosgene).

The equivalent diameter of the flow channel in the joining part (M1) is preferably 0.1 to 30 mm from the viewpoint of further improving the mixing performance.

The material of the joining part (M1) is not particularly limited, and a material consisting of, for example, a perfluoroalkoxy alkane (PFA), Teflon (registered trade name), an aromatic polyether ketone-based resin, stainless steel, copper or a copper alloy, nickel or a nickel alloy, titanium or a titanium alloy, quartz glass, lime soda glass, or the like can be used.

A commercially available product can be widely used as the above cross-shaped connector, and the following can be used as the commercially available product, for example; a cross-shaped connector manufactured by Upchurch Scientific Inc.; a union cross manufactured by Swagelok Company; a 4-way joint manufactured by TOKYO RIKAKIKAI Co, Ltd., a SUS cross mixer manufactured by IDEX CORPORATION, or the like.

In the configuration of FIG. 1, the phosgene solution, the active hydrogen-containing compound solution, and the tertiary amine solution are simultaneously mixed at the joining part (M1). This configuration is preferable in that phosgene can be efficiently consumed by the active hydrogen-containing compound before a side reaction between the phosgene and the tertiary amine occurs.

<Flow Channel (III)>

The flow channel (III) is a flow channel in which the tertiary amine solution introduced from the introduction port (iC) is supplied to the joining part (M1). The flow channel (III) is preferably set to have an equivalent diameter of 0.1 to 50 mm. In a case where the equivalent diameter of the flow channel (III) is set to 0.1 mm or more, it is possible to suppress an increase in pressure during liquid feeding, and it is possible to suppress the clogging of the flow channel even in a case where an insoluble matter is generated. In addition, in a case where the equivalent diameter of the flow channel (III) is set to 50 mm or less, it is possible to suitably control the liquid temperature at the time of being introduced into joining part (M1). The equivalent diameter of the flow channel (III) is more preferably 0.5 to 30 mm and still more preferably 1 to 20 mm.

The length of the flow channel (III) is not particularly limited, and for example, it can be constituted of a tube having a length of about 10 cm to 15 m (preferably 30 cm to 10 m).

The material of the tube is not particularly limited, and the tube of the material exemplified in the above flow channel (I) can be used.

The flow speed for introducing the tertiary amine solution from the introduction port (iC) is not particularly limited, and it can be appropriately set depending on the intended purpose in consideration of the equivalent diameter of the flow channel, the concentration of the tertiary amine solution, the concentration of the triphosgene solution, the concentration of the active hydrogen-containing compound solution, the introduction flow rate of the triphosgene solution, the introduction flow rate of the active hydrogen-containing compound solution, and the like. For example, 0.1 to 5,000 mL/minutes (min) is preferable, 0.5 to 3,000 mL/min is more preferable, and 1 to 3,000 mL/min is still more preferable. In a case where the introduction flow rate of the tertiary amine solution is set within the above range, side reactions can be suppressed and the purity can be improved.

—Tertiary Amine Solution—

The tertiary amine solution that is allowed to flow inside the flow channel (III) is generally a solution obtained by dissolving a tertiary amine in a solvent. The solvent contained in the tertiary amine solution is generally an organic solvent. As the organic solvent, those exemplified as the solvent of the above-described triphosgene solution can be preferably used. The tertiary amine solution and the triphosgene solution may use the same solvent, or the kinds of solvents thereof may be different from each other. In a case where the kinds of solvents thereof are different from each other, it is preferable to use solvents that are compatible with each other (solvents that do not phase-separate in a case of being mixed).

(Tertiary Amine)

In the present invention, the term "tertiary amine" is used in a broader sense than usual. That is, all amines in which a hydrogen atom is not bonded to a nitrogen atom (amines in which all three bonding sites of the nitrogen atom are bonded to an atom other than the hydrogen atom) are included in the "tertiary amine". For example, a compound having an aromatic ring (for example, a pyridine ring, a pyridazine ring, a pyrimidine ring, a pyrazine ring, a 2H-pyrrole ring, an oxazole ring, an isoxazole ring, or a thiazole ring, an isothiazole ring) which has a nitrogen atom as a ring-constituting atom and in which the nitrogen atom which is a ring-constituting atom does not have an active hydrogen atom is the tertiary amine in the present invention. In addition, a configuration in which in a compound having a pyrrole ring, a pyrazole ring, an imidazole ring, or the like, which is an aromatic ring, a hydrogen atom possessed by the nitrogen atom which is a ring-constituting atom is substituted with another substituent is also the tertiary amine in the present invention.

The tertiary amine of the tertiary amine solution preferably does not have active hydrogen even in the structural part other than the amino group. That is, it is preferably non-reactive with phosgene.

The tertiary amine of the tertiary amine solution preferably has a cyclic structure from the viewpoint of suppressing the clogging of the flow channel. The cyclic structure may be an aromatic ring or an alicyclic ring. This cyclic structure is preferably a 5-membered ring or a 6-membered ring. In addition, this cyclic structure may be a fused-ring structure (a structure in which a ring selected from a 5-membered ring and a 6-membered ring is fused).

Preferred examples of the cyclic structure that can be included in the tertiary amine include a ring having a nitrogen atom as a ring-constituting atom. Specific examples thereof include a morpholine ring, a piperazine ring, a piperidine ring, a 2-pyrroline ring, a pyrrolidine ring, a 2-imidazoline ring, an imidazolidine ring, a pyrazoline ring, a pyrazolidine ring, a pyridine ring, a pyridazine ring, a pyrimidine ring, a pyrazine ring, a 2H-pyrrole ring, an oxazole ring, an isoxazole ring, a thiazole ring, an isothiazole ring, a pyrrole ring, a pyrazole ring, an imidazole ring, an indole ring, an isoindole ring, a 1H-indole ring, a quinoline ring, an isoquinoline ring, a cinnoline ring, a phthalazine ring, a quinazoline ring, a quinoxaline ring, a 1,8-naphthyridine ring, a purine ring, a pteridine ring, an indolizine ring, a carbazole ring, an acridine ring, a phenazine ring, a phenanthridine ring, a 1,10-phenanthroline ring, a phenoxazine ring, and a quinuclidine ring.

The cyclic structure that can be included in the tertiary amine is preferably a ring selected from a morpholine ring, a pyridine ring, a piperazine ring, a piperidine ring, a pyrrolidine ring, an imidazole ring, a quinoline ring, and a thiomorpholine ring, and it is more preferably a ring selected from a morpholine ring and a pyridine ring.

The tertiary amine of the tertiary amine solution preferably has 6 to 40 carbon atoms, more preferably 6 to 30 carbon atoms, and still more preferably 6 to 26 carbon atoms.

The molecular weight of the tertiary amine that is used in the present invention is preferably 100 to 700 and more preferably 100 to 450.

Specific examples of the above tertiary amine are shown below.

1

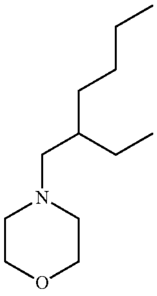

2

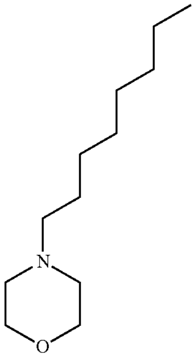

3

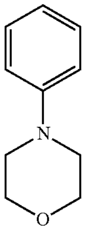

-continued

4

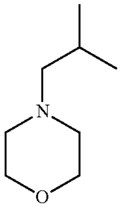

5

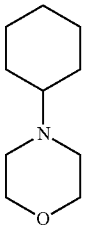

6

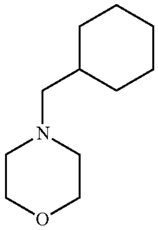

7

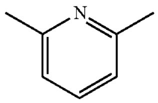

8

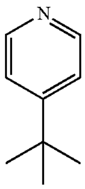

9

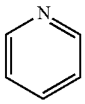

10

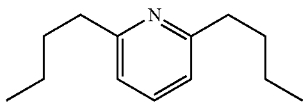

11

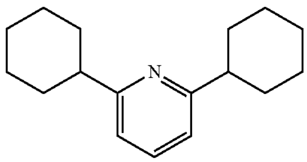

-continued
12
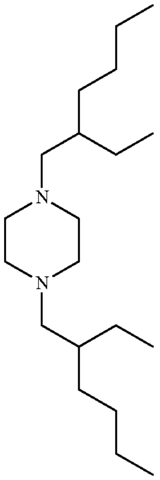
13
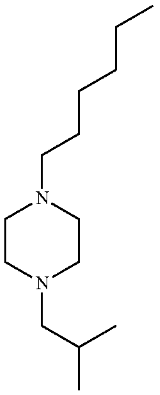
14
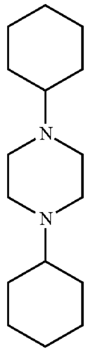
15
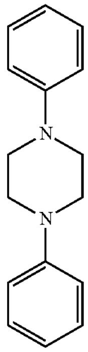
-continued
16
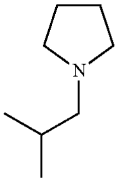
17
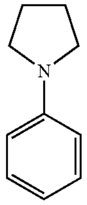
18
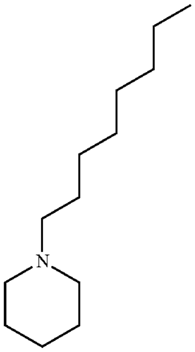
19
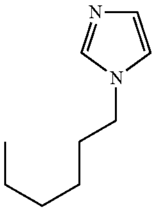
20
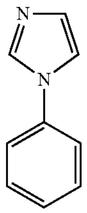
21
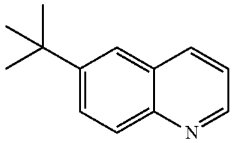
22
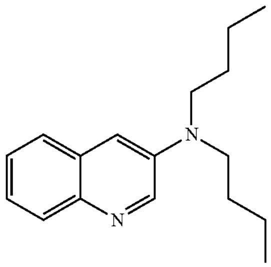

-continued

23

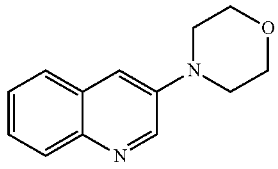

24

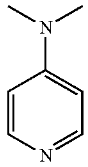

25

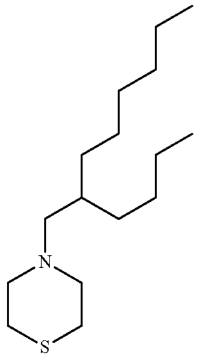

26

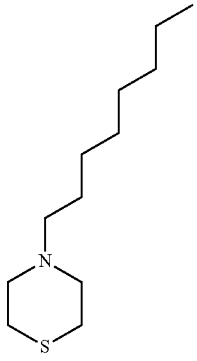

27

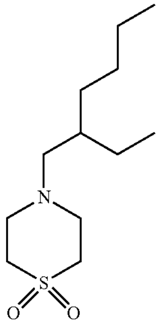

28

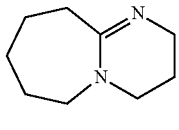

29

$N(C_4H_9)_3$

-continued

30

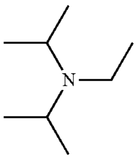

The content of the tertiary amine in the tertiary amine solution is not particularly limited, and it is appropriately adjusted in consideration of the introduction flow rate of the tertiary amine solution, the concentration of the triphosgene solution, the introduction flow rate of the triphosgene solution, the concentration of the active hydrogen-containing compound solution, the introduction flow rate of the active hydrogen-containing compound solution, and the like. The content of the tertiary amine in the tertiary amine solution can be, for example, 0.03 to 10 M (mol/liter), and it is preferably 0.05 to 7 M and more preferably 0.1 to 5 M.

The temperature of the flow channel (III) is preferably set to be lower than the boiling point of the solvent used to prepare the tertiary amine solution. For example, it can be set to −60° C. to 80° C., and it is preferably −20° C. to 30° C. and still more preferably −10° C. to 20° C.

<Reaction Pipe (IV)>

After the phosgene solution and the active hydrogen-containing compound solution are joined and mixed at the joining part (M1), they flow into the reaction pipe (IV), which is a reaction flow channel, and while they flow downstream inside the reaction pipe (IV), phosgene reacts with an active hydrogen-containing compound in the presence of the tertiary amine. In the present specification, the reaction pipe (IV) may be referred to as a flow channel (IV).

The form of the reaction pipe (IV) is not particularly limited, and a tube is generally used. The preferred material of the reaction pipe (IV) is the same as the preferred material of the flow channel (I) described above. In addition, the reaction time can be adjusted by setting the equivalent diameter and the length of the reaction pipe (IV), the flow rate of the liquid feeding pump, and the like. Generally, the equivalent diameter of the reaction pipe (IV) is preferably 0.1 to 50 mm, more preferably 0.2 to 20 mm, still more preferably 0.4 to 15 mm, even still more preferably 0.7 to 12 mm, and even further still more preferably 1 to 10 mm. In addition, the length of the reaction pipe (IV) is preferably 0.5 to 50 m and more preferably 1 to 30 m.

At the time of feeding liquids of raw materials, the molar ratio between triphosgene, the active hydrogen-containing compound, and the tertiary amine is appropriately set depending on the target reaction. For example, it can be set to [triphosgene]:[active hydrogen-containing compound]:[tertiary amine]=0.1 to 2:1:0.6 to 12, and it is preferably [triphosgene]:[active hydrogen-containing compound]:[tertiary amine]=0.35 to 1.5:1:2 to 9.

The temperature of the reaction pipe (IV) is preferably set to be lower than a boiling point of a solvent of which the boiling point is lowest among solvents in the reaction solution that flows inside the reaction pipe (IV) (in a case where the solvent is one kind, it is preferably lower than the boiling point of this one kind of solvent). For example, the temperature of the reaction pipe (IV) can be set to −60° C. to 80° C., and it is preferably −20° C. to 30° C. and still more preferably −10° C. to 20° C.

Another embodiment of the flow type reaction system for carrying out the production method of the present invention will be described with reference to FIG. 2.

Figure 2:
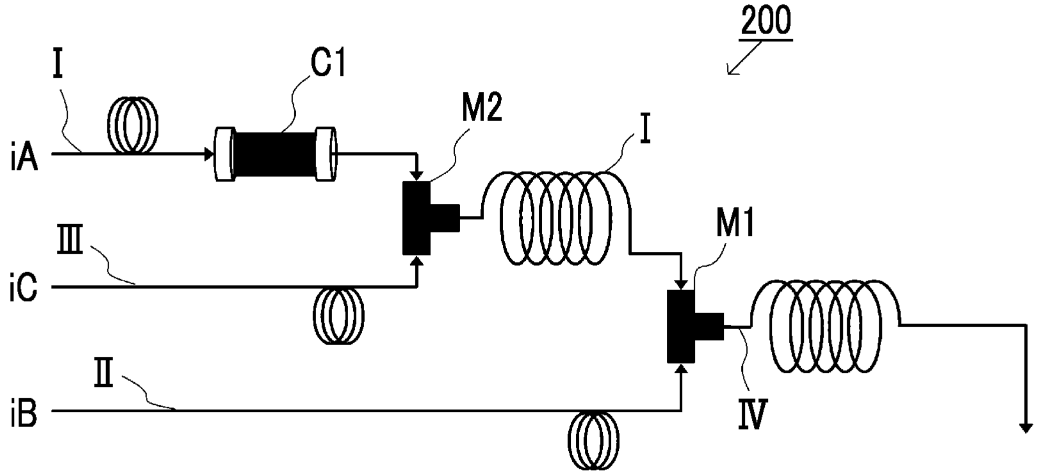
FIG. 2 is an illustrative view illustrating an outline of another embodiment of a flow type reaction system according to the embodiment of the present invention.

A flow type reaction system (200) illustrated in FIG. 2 is different from the embodiment of FIG. 1 in that the flow channel (III) through which a tertiary amine solution flows is connected downstream of a portion (that is, a portion in the middle of the flow channel (I), where the portion is located downstream of the column (C1)) of the flow channel (I) into which the triphosgene solution is introduced, where the portion is the place where the column (C1) is installed. As a result, in the embodiment of FIG. 2, it is not necessary to provide a connection port of the flow channel (III) at the joining part (M1), and thus a T-shaped connector is used at the joining part (M1). The constitution other than the above is the same as that described in the configuration of FIG. 1. n addition, in association with the configuration in which the flow channel (III) is joined in the middle of the flow channel (I), the equivalent diameter of the flow channel and the like can be appropriately adjusted as necessary.

In the embodiment illustrated in FIG. 2, the equivalent diameter of the flow channel in the joining part (M1) is preferably 0.2 to 50 mm from the viewpoint of further improving the mixing performance.

In the embodiment illustrated in FIG. 2, the material of the joining part (M1) is not particularly limited, and a material consisting of, for example, a perfluoroalkoxy alkane (PFA), Teflon (registered trade name), an aromatic polyether ketone-based resin, stainless steel, copper or a copper alloy, nickel or a nickel alloy, titanium or a titanium alloy, quartz glass, lime soda glass, or the like can be used.

A commercially available T-shaped or Y-shaped mixer can be used for the joining part (M1) illustrated in FIG. 2. Examples thereof include Microglass Reactor manufactured by Microglass; Cytos manufactured by CPC Systems Ltd.; YM-1 and YM-2 type mixers manufactured by Yamatake Co., Ltd.; a mixing tee and a tee (T-shaped connectors) manufactured by SHIMADZU GLC Ltd.; a mixing tee and a tee (T-shaped connectors) manufactured by GL Sciences Inc.; a mixing tee and a tee (T-shaped connectors) manufactured by Upchurch Scientific Inc.; a mixing tee and a tee (T-shaped connectors) manufactured by Valco Instruments Co. Inc.; a T-shaped connector manufactured by Swagelok Company; and a SUS T-type mixer manufactured by IDEX CORPORATION. Any one of these can be used in the present invention.

<Joining Part M2>

In the embodiment illustrated in FIG. 2, as described above, the flow channel (III) through which the tertiary amine solution flows is connected in the middle of the flow channel (I) into which the triphosgene solution is introduced. That is, the phosgene solution and the tertiary amine solution are mixed in advance in the flow channel (I), and then the mixed solution and the active hydrogen-containing compound solution are joined.

In FIG. 2, the joining part (M2) between the flow channel (III) and the flow channel (I) is provided downstream of the column of the flow channel (I). However, the present invention is not limited to this configuration, and for example, the flow channel (III) may be joined upstream of the column of the flow channel (I).

The connection method between the flow channel (I) and the flow channel (III) (the form of the joining part (M2)) is not particularly limited, and for example, the above-described T-shaped or Y-shaped connector can be used.

In the embodiments of FIGS. 1 and 2, the retention time (the reaction time) of the reaction solution (joining solution) in the reaction flow channel (IV) is preferably set to 2 seconds or more, more preferably 3 to 600 seconds, and still more preferably 5 to 200 seconds. In a case where the reaction time is shortened to some extent, side reactions can be suppressed more effectively.

According to the production method according to the embodiment of the present invention, triphosgene is converted into phosgene with high efficiency by the action of the solid catalyst in the flow channel (I). As a result, impurities are hardly generated in the subsequent reaction with the active hydrogen-containing compound in the presence of the tertiary amine, and a target carbonyl compound can be obtained with high purity.

The present invention has been described together with the preferred embodiments thereof; however, the present invention is not limited to the above embodiments except for the matters specified in the present invention.

For example, for the flow type reaction according to the embodiment of the present invention, a flow type reaction system can be widely used, where the flow type reaction system includes;

a first flow channel through which triphosgene flows; a second flow channel through which an active hydrogen-containing compound solution flows; a joining part at which the first flow channel and the second flow channel are joined; and a reaction pipe which is connected downstream of the joining part, in which a solid catalyst that converts triphosgene into phosgene is immobilized in at least a part of the first flow channel.

The reaction conditions, the pipe connection, the timing of addition of the tertiary amine, and the like may be appropriately adjusted depending on the intended purpose.

The above flow type reaction system preferably has a configuration in which the third flow channel into which the tertiary amine solution is introduced is joined at the joining part at which the first flow channel and the second flow channel are joined or on the side upstream of this joining part (that is, at the first flow channel or the second flow channel).

In the flow type reaction according to the embodiment of the present invention, it is also preferable to arrange a dehydrating agent (for example, a molecular sieve) in at least a part of the flow channel. In a case where the water content in the reaction solution is removed, side reactions can be suppressed more effectively. This dehydrating agent is preferably arranged, for example, upstream of the portion at which each of the flow channels is joined.

In addition, it is preferable that the dehydrating agent is immobilized in the flow channel. The configuration of this immobilization is not particularly limited, and for example, the same method as the immobilization of the solid catalyst described above can be adopted.

Figure 5:
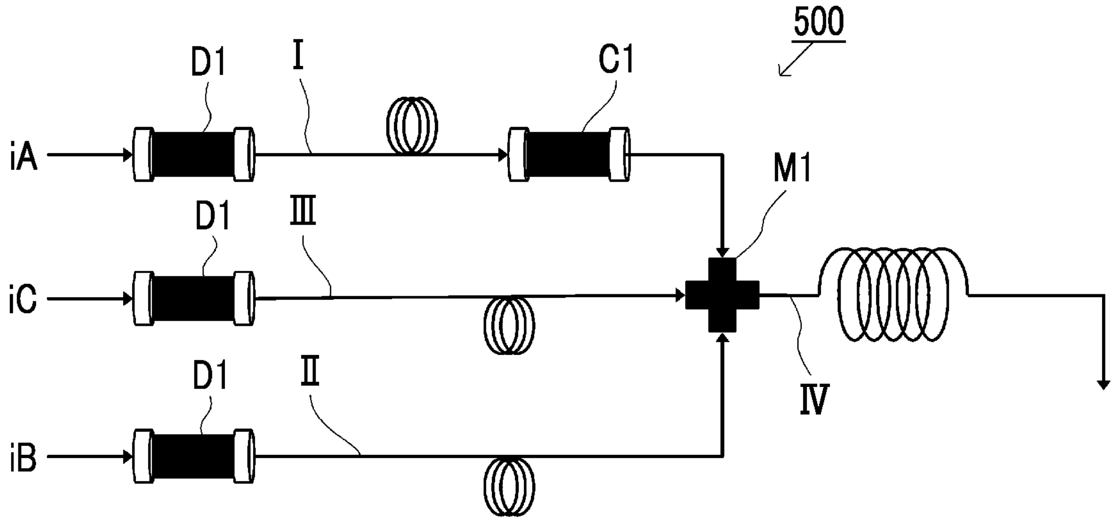
FIG. 5 is an illustrative view illustrating an outline of still another embodiment of a flow type reaction system according to the embodiment of the present invention.

An example of such an embodiment is illustrated in FIG. 5. n the flow type reaction system illustrated in FIG. 5, columns (D1) filled with a dehydrating agent are provided at the introduction ports (iA), (iB), and (iC). As a result, the flow type reaction can be carried out in a state where the water content is sufficiently removed, and thus the purity of the reaction product to be obtained can be further increased.

In addition, in the flow type reaction according to the embodiment of the present invention, an acid trapping agent can be arranged in at least a part of the flow channel.

The present invention will be described in more detail based on Examples; however, the present invention is not limited to these Examples.

EXAMPLES

Example 1

An isocyanate compound was synthesized using the flow type reaction system 100 having the constitution illustrated in FIG. 1. The reaction scheme of this synthesis reaction is shown below. In the scheme below, "Ph" is phenyl, and $NR_3$ is a tertiary amine.

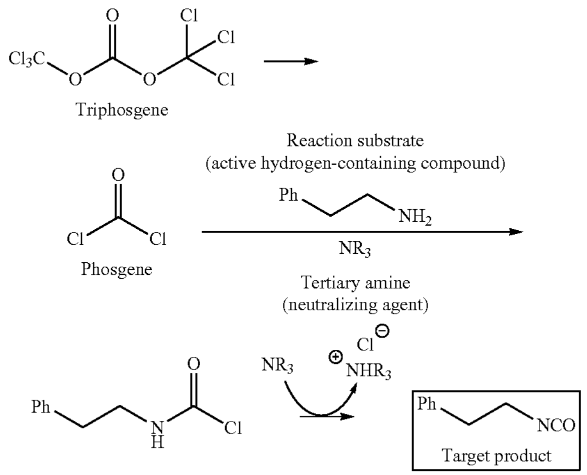

The specific reaction conditions are as follows.

Liquid Feeding Pump (not Illustrated in the Drawing):

All liquid feeding pumps used were PU716B and PU718 manufactured by GL Sciences Inc., and a pulse damper HPD-1, a back pressure valve (44-2361-24) manufactured: by NIHON TESCON Co., Ltd., and a relief valve RHA (4 MPa) manufactured by IBS COMPANY were sequentially installed on the side of the flow outlet port.

Temperature Control:

All of the flow channels (I) to (IV) and the joining part M1 were immersed in water set at 10° C.

Flow Channels (I) to (IV):

All flow channels used were a SUS316 tube having an outer diameter of 1/16 inch and an inner diameter of 1.0 mm. The length of each of the flow channels is as follows.

Flow channel (I): 0.5 m+a column length of 50 mm described later

Flow channel (II): 0.5 m

Flow channel (III): 0.5 m

Flow channel (IV): 1.0 m

Column (C1) Filled with Solid Catalyst:

A copolymer of 4-vinylpyridine and divinylbenzene (4-vinylpyridine (Vpy)/divinylbenzene (DVB)=98/2 (molar ratio), manufactured by Sigma-Aldrich Co., LLC) was used as the solid catalyst.

A SUS column container having an inner diameter of 10 mm and a length of 50 mm was filled with 1.66 g of the above solid catalyst to prepare a column filled with a solid catalyst.

Joining Part (M1) (Cross-Shaped Connector):

A SUS cross mixer manufactured by IDEX CORPORATION having an inner diameter of 0.5 mm was used.

Triphosgene Solution:

A triphosgene solution (triphosgene concentration: 0.0661 M) obtained by dissolving triphosgene in methylene chloride was prepared.

Active Hydrogen-Containing Compound Solution:

A phenethylamine solution (phenethylamine concentration: 0.132 M) obtained by dissolving phenethylamine in methylene chloride was prepared.

Tertiary Amine Solution:

An N-(2-ethylhexyl) morpholine solution (N-(2-ethylhexyl) morpholine concentration: 0.529M) obtained by dissolving N-(2-ethylhexyl) morpholine in methylene chloride was prepared.

Liquid Feeding Conditions:

Triphosgene solution: 1.0 mL/min

Active hydrogen-containing compound solution: 1.0 mL/min

Tertiary amine solution: 1.0 mL/min

Purity of Reaction Product (Isocyanate Compound):

A reaction solution was collected from the outlet port (most downstream) of the flow channel (IV), diluted 500-fold with a reaction solvent (methylene chloride in Example 1), and the diluted sample was analyzed by gas chromatography under the following conditions to measure the purity. The results are shown in the table below. In the table below, ">97" means that the purity is more than 97% by mass, and "<10" means that the purity is less than 10% by mass.

—Analysis Conditions—

Measuring equipment: GC-3200 (manufactured by GL Sciences Inc.)

Column: APS-1,000 (Teflon, 3φ×6 m, manufactured by GL Sciences Inc.)

Column temperature: 250° C.

Carrier gas: Hydrogen (hydrogen gas generator: HG260B, manufactured by GL Sciences Inc.)

Injection volume: 1 μL

The results are shown in the table below.

Evaluation of Flow Channel Clogging:

A pressure gauge was installed in the middle of the flow channel between the tertiary amine solution introduction port (iC) and the joining part (M1) (that is, inside the flow channel (III)), and the pressure after 1 hour passed at the time when the liquid feeding became stable and the reaction was in a steady state, was evaluated as evaluation "A" in a case of less than 0.05 MPa, as evaluation "B" in a case of 0.05 MPa or more and less than 0.1 MPa, and as evaluation "C" in a case of 0.1 MPa or more. The results are shown in the table below.

Examples 2 to 33 and Comparative Examples 1 and 2

Flow type reactions were carried out in the same manner as in Example 1 except that the kinds of flow type reaction systems (systems illustrated in FIGS. 1 to 4), solid catalysts with which columns were filled, solvents, and tertiary amines (the matching between numbers and chemical structures of tertiary amines is as described above) were as shown in the table below. The results are shown in the table below.

The abbreviations in the table below are as follows.

"Vpy/DVB=98/2": Solid catalyst having a Vpy/DVB molar ratio of 98/2 (manufactured by Sigma-Aldrich Co., LLC)

"Vpy/DVB=75/25": Solid catalyst having a Vpy/DVB molar ratio of 75/25 (manufactured by Sigma-Aldrich Co., LLC)

"Activated carbon": Pulverized, particle size: 0.2 to 1 mm (manufactured by FUJIFILM Wako Pure Chemical Corporation)

"QuadraPure BDZ": Surface imidazole group-modified polystyrene resin (manufactured by Sigma-Aldrich Co., LLC)

Figure 3:
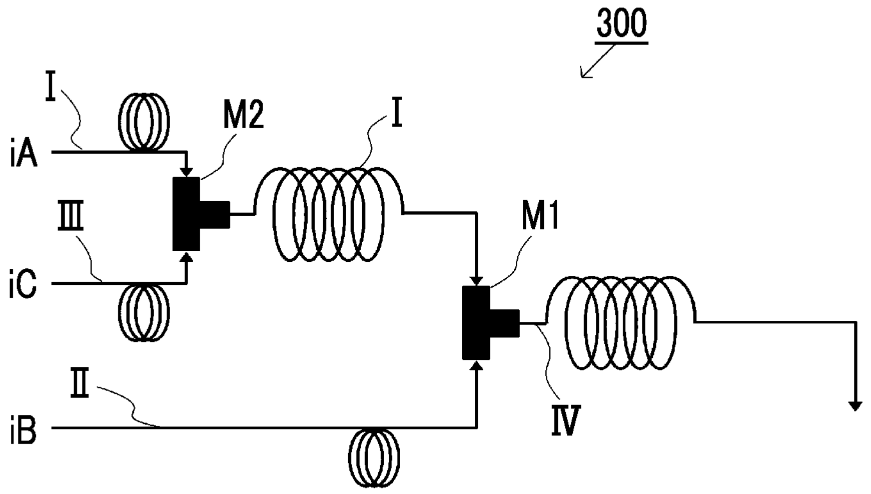
FIG. 3 is an illustrative view illustrating an outline of one embodiment of a flow type reaction system which is different from the present invention.
Figure 4:
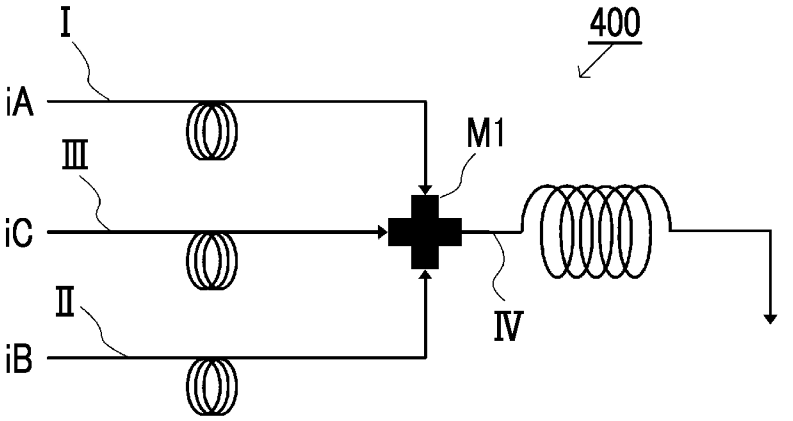
FIG. 4 is an illustrative view illustrating an outline of another embodiment of a flow type reaction system which is different from the present invention.

In the flow type reaction systems (200, 300, 400) of FIGS. 2 to 4, a SUS316 tube having an outer diameter of 1/16 inch and an inner diameter of 1.0 mm was used as the flow channels (I) to (IV). It is noted that in the configuration of FIG. 2, the column (C1) was similarly provided in the flow channel (I) as in Example 1 (FIG. 1).

In each of the flow type reaction systems (200, 300) of FIGS. 2 and 3, SUS T-type mixers having an inner diameter of 0.5 mm, manufactured by IDEX CORPORATION, were used as two T-shaped connectors (M1, M2).

In the flow type reaction system (200) of FIG. 2, the length of the flow channel (I) on the side upstream of the joining part between the flow channel (I) and the flow channel (III) was set to a tube length of 0.5 m+a column length of 50 mm, and the length on the side downstream of the joining part was set to 0.5 m (that is, the length of the entire flow channel (I) was set to 1.0 m+a column length of 50 mm). The lengths of the flow channel (II), the flow channel (III), and the flow channel (IV) are respectively the same as the lengths of the flow channel (II), the flow channel (III), and the flow channel (IV) in the flow type reaction system of FIG. 1.

In the flow type reaction system (300) of FIG. 3, the length of the flow channel (I) on the side upstream of the joining part between the flow channel (I) and the flow channel (III) was set to 0.5 m, and the length on the side downstream of the joining part between the flow channel (I) and the flow channel (III) was set to 1.0 m. The lengths of the flow channel (II), the flow channel (III), and the flow channel (IV) are respectively the same as the lengths of the flow channel (II), the flow channel (III), and the flow channel (IV) in the flow type reaction system of FIG. 1.

In FIG. 4, a SUS cross mixer having an inner diameter of 0.5 mm, manufactured by IDEX CORPORATION, was used as the cross-shaped connector that constitutes the joining part (M1). The length of the flow channel (I) is set to 0.5 m, and the lengths of the flow channel (II), the flow channel (III), and the flow channel (IV) are respectively the same as the lengths of the flow channel (II), the flow channel (III), and the flow channel (IV) in the flow type reaction system of FIG. 1.

TABLE 1

| | Solid catalyst | Tertiary amine | Solvent | Flow type reaction system | Evaluation result: Purity (% by mass) | Evaluation result: Clogging property |
|---|---|---|---|---|---|---|
| Example 1 | Vpy/DVB = 98/2 | 1 | Methylene chloride | FIG. 1 | >97 | A |
| Example 2 | Vpy/DVB = 98/2 | 1 | Methylene chloride | FIG. 2 | >97 | A |
| Example 3 | Vpy/DVB = 98/2 | 1 | Toluene | FIG. 1 | >97 | A |
| Example 4 | Activated carbon | 1 | Methylene chloride | FIG. 1 | 89 | A |
| Example 5 | Vpy/DVB = 98/2 | 2 | Methylene chloride | FIG. 1 | 95 | A |
| Example 6 | Vpy/DVB = 98/2 | 3 | Xylene | FIG. 1 | 82 | A |
| Example 7 | Vpy/DVB = 98/2 | 4 | Methylene chloride | FIG. 1 | 91 | A |
| Example 8 | Vpy/DVB = 98/2 | 5 | Methylene chloride | FIG. 2 | 89 | A |
| Example 9 | Vpy/DVB-75/25 | 6 | Toluene | FIG. 1 | 92 | A |
| Example 10 | Vpy/DVB = 98/2 | 7 | Methylene chloride | FIG. 1 | >97 | A |
| Example 11 | Vpy/DVB = 75/25 | 8 | Mesitylene | FIG. 1 | >97 | A |
| Example 12 | Vpy/DVB = 98/2 | 9 | Methylene chloride | FIG. 1 | 79 | B |
| Example 13 | Vpy/DVB = 75/25 | 10 | Acetonitrile | FIG. 1 | >97 | A |
| Example 14 | Vpy/DVB = 98/2 | 11 | Toluene | FIG. 1 | 77 | A |
| Example 15 | QuadraPure BDZ | 12 | Chlorobenzene | FIG. 2 | 90 | A |
| Example 16 | Vpy/DVB = 98/2 | 13 | Methylene chloride | FIG. 1 | 81 | A |
| Example 17 | Vpy/DVB = 98/2 | 14 | o-dichlorobenzene | FIG. 1 | 83 | A |
| Example 18 | Vpy/DVB = 75/25 | 15 | Methylene chloride | FIG. 1 | 78 | A |
| Example 19 | Vpy/DVB = 98/2 | 16 | Tetrahydrofuran | FIG. 1 | 76 | B |
| Example 20 | Vpy/DVB = 98/2 | 17 | Chlorobenzene | FIG. 1 | 76 | A |
| Example 21 | QuadraPure BDZ | 18 | Methylene chloride | FIG. 1 | 82 | A |
| Example 22 | Vpy/DVB = 98/2 | 19 | Chlorobenzene | FIG. 1 | 74 | A |
| Example 23 | Vpy/DVB = 98/2 | 20 | Toluene | FIG. 1 | 72 | A |
| Example 24 | Vpy/DVB = 98/2 | 21 | Toluene | FIG. 1 | 76 | A |
| Example 25 | Vpy/DVB = 98/2 | 22 | Methylene chloride | FIG. 1 | 73 | A |
| Example 26 | Activated carbon | 23 | Mesitylene | FIG. 1 | 87 | A |
| Example 27 | Vpy/DVB = 98/2 | 24 | Methylene chloride | FIG. 1 | 62 | B |
| Example 28 | Vpy/DVB = 75/25 | 25 | Methylene chloride | FIG. 1 | 70 | A |
| Example 29 | Vpy/DVB = 98/2 | 26 | Xylene | FIG. 2 | 64 | A |
| Example 30 | Vpy/DVB = 98/2 | 27 | Methylene chloride | FIG. 1 | 58 | A |
| Example 31 | Vpy/DVB = 75/25 | 28 | Toluene | FIG. 2 | 55 | A |
| Example 32 | Vpy/DVB = 75/25 | 29 | Methylene chloride | FIG. 2 | 79 | A |
| Example 33 | Vpy/DVB = 98/2 | 30 | Toluene | FIG. 1 | 53 | A |
| Comparative Example 1 | — | 30 | Toluene | FIG. 1 | 19 | A |
| Comparative Example 2 | — | 30 | Toluene | FIG. 2 | <10 | C |

As shown in Table 1 above, in Comparative Examples 1 and 2 using a flow type reaction system in which the solid catalyst was not immobilized in the flow channel (I), the purity of the obtained target reaction product could not be increased to a desired purity (the comparison between Comparative Examples 1 and 2 and Example 33). It is noted that in the flow type reaction systems of FIGS. 3 and 4, which are used in Comparative Examples 1 and 2, the tertiary amine functions not only as a neutralizing agent but also as a catalyst for converting triphosgene into phosgene.

On the other hand, in a case where a flow type reaction system in which the solid catalyst for converting triphosgene into phosgene was immobilized inside the flow channel (I) was applied, the purity of the obtained target reaction product was significantly increased (Examples 1 to 33). This result is obtained as a result of dramatically increasing the efficiency of converting triphosgene into phosgene by immobilizing the solid catalyst in the flow channel (I).

Example 34

A flow type reaction was carried out in the same manner as in Example 33 except that the flow type reaction system illustrated in FIG. 5 was used. In the flow type reaction system of FIG. 5, in the system of FIG. 1, the column (D1) filled with a dehydrating agent is provided at the introduction port of each of the flow channels (I), (II), and (III). This column container is made of SUS having an inner diameter of 20 mm and a length of 100 mm, and it is filled with 9.3 g of Molecular Sieve 4A (manufactured by FUJIFILM Wako Pure Chemical Corporation) as a dehydrating agent.

In this Example 34, the purity of the target reaction product obtained was 64%. That is, it can be seen that the purity of the obtained reaction product is further increased by arranging a dehydrating agent (the comparison between Example 33 and Example 34).

Examples 35 to 38

Using the flow type reaction system illustrated in FIG. 1, flow type reactions were carried out in the same manner as in Example 1, where the kinds of tertiary amines used were as shown in the table below. The reaction was carried out continuously for 20 hours, during which the occurrence of temporal clogging was examined. The evaluation standards for clogging were the same as above. In these Examples 35 to 38, toluene was used as the solvent. The results are shown in the table below.

TABLE 2

| | Tertiary amine | Flow type reaction system | Reaction time After 1 hour | After 5 hours | After 10 hours | After 20 hours |
|---|---|---|---|---|---|---|
| Example 35 | 1 | FIG. 1 | A | A | A | A |
| Example 36 | 7 | FIG. 1 | A | A | A | A |
| Example 37 | 18 | FIG. 1 | A | A | A | B |
| Example 38 | 30 | FIG. 1 | A | B | B | C |

As shown in Table 2 above, it can be seen that in a case where a tertiary amine having a cyclic structure is applied, the temporal clogging of the flow channel can be suppressed, and thus a flow type reaction can be stably carried out for a long time (the comparison between Examples 35 to 37 and Example 38).

Examples 39 to 54

Flow type reactions were carried out in the same manner as in Example 1 except that the kinds of flow type reaction systems (systems illustrated in FIGS. 1 to 4), active hydrogen-containing compounds (primary amines), solid catalysts with which columns were filled, solvents, and tertiary amines (the matching between numbers and chemical structures of tertiary amines is as described above) were as shown in the table below. The reaction was carried out continuously for 20 hours, during which the purity of the product and the occurrence of temporal clogging were examined. The evaluation standards for clogging were the same as above. The results are shown in the table below.

The abbreviations in the table below are the same as above.

TABLE 3

| | Primary amine | Solid catalyst | Tertiary amine | Solvent | Flow type system | Product | Evaluation result Purity (% by mass) | Clogging property |
|---|---|---|---|---|---|---|---|---|
| Example 39 | 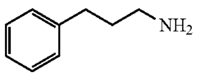 | Vpy/DVB = 98/2 | 1 | Methylene chloride | FIG. 1 | 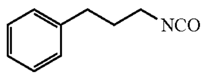 | >97 | A |
| Example 40 | 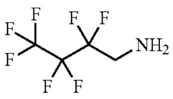 | Vpy/DVB = 98/2 | 1 | Methylene chloride | FIG. 1 | 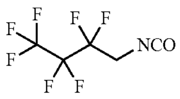 | 93 | A |
| Example 41 | 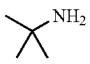 | Vpy/DVB = 98/2 | 1 | Methylene chloride | FIG. 1 | 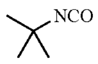 | 85 | A |
| Example 42 | 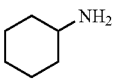 | Vpy/DVB = 75/25 | 1 | Methylene chloride | FIG. 1 | 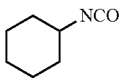 | 89 | A |
| Example 43 | 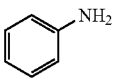 | Vpy/DVB = 98/2 | 7 | Methylene chloride | FIG. 1 | 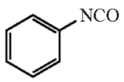 | 91 | A |
| Example 44 | 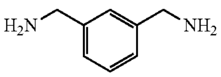 | Vpy/DVB = 98/2 | 7 | Toluene | FIG. 1 | 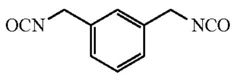 | 89 | A |

TABLE 3-continued

| | Primary amine | Solid catalyst | Tertiary amine | Solvent | Flow type system | Evaluation result Product | Purity (% by mass) | Clogging property |
|---|---|---|---|---|---|---|---|---|
| Example 45 | 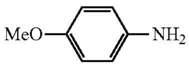 | Vpy/DVB = 98/2 | 1 | Methylene chloride | FIG. 1 | 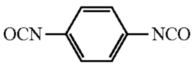 | >97 | A |
| Example 46 | 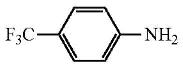 | Vpy/DVB = 98/2 | 1 | Methylene chloride | FIG. 1 | 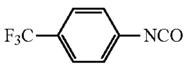 | >97 | A |
| Example 47 | 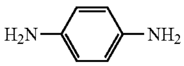 | Vpy/DVB = 98/2 | 1 | Methylene chloride | FIG. 1 | 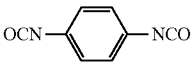 | 91 | A |
| Example 48 | 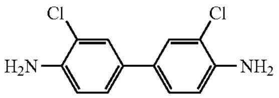 [SMILES: Nc1ccc(-c2ccc(N)c(Cl)c2)cc1Cl] | Vpy/DVB = 98/2 | 2 | Methylene chloride | FIG. 1 | 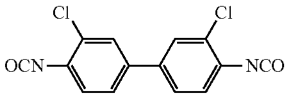 | 78 | A |
| Example 49 | 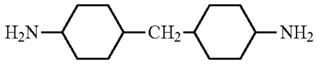 | Vpy/DVB = 98/2 | 7 | Chlorobenzene | FIG. 1 | 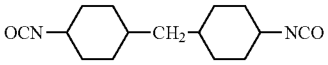 | 82 | A |
| Example 50 | 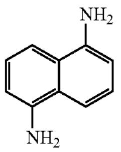 | Vpy/DVB = 98/2 | 7 | o-dichlorobenzene | FIG. 1 | 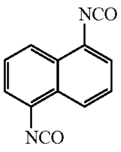 | 84 | B |
| Example 51 | 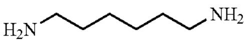 | Vpy/DVB = 98/2 | 7 | Chlorobenzene | FIG. 1 | 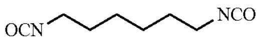 | >97 | A |
| Example 52 | 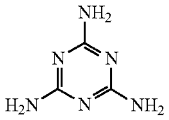 | Vpy/DVB = 98/2 | 2 | Methylene chloride/o-dichlorobenzene (1/1) | FIG. 1 | 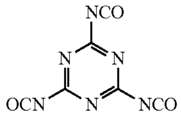 | 78 | B |
| Example 53 | 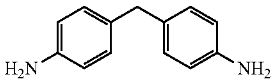 [SMILES: Nc1ccc(Cc2ccc(N)cc2)cc1] | Vpy/DVB = 98/2 | 7 | o-dichlorobenzene | FIG. 1 | 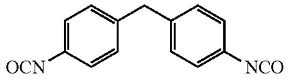 | 91 | A |
| Example 54 | 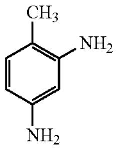 | Vpy/DVB = 98/2 | 1 | Chlorobenzene | FIG. 1 | 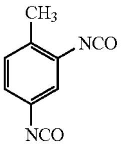 | 92 | A |

Examples 55 to 58

Using the flow type reaction system illustrated in FIG. 1, flow type reactions were carried out in the same manner as in Example 1 by using alcohol compounds shown in the table below as the active hydrogen-containing compound, where the kinds of solid catalysts with which columns were filled, solvents, and tertiary amines (the matching between numbers and chemical structures of tertiary amines is as described above) were as shown in the table below. The reaction was carried out continuously for 20 hours, during which the purity of the product and the occurrence of temporal clogging were examined. The evaluation standards for clogging were the same as above. The results are shown in the table below.

The abbreviations in the table below are the same as above.

TABLE 4

| | | | | | | Evaluation result | | |
|---|---|---|---|---|---|---|---|---|
| | Alcohol | Solid catalyst | Tertiary amine | Solvent | Flow type reaction system | Product | Purity (% by mass) | Clogging property |
| Example 55 | 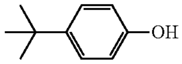 | Vpy/DVB = 98/2 | 1 | Methylene chloride | FIG. 1 | 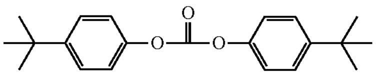 | 81 | A |
| Example 56 | 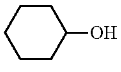 | Vpy/DVB = 98/2 | 1 | Methylene chloride | FIG. 1 | 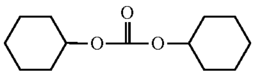 | 83 | A |
| Example 57 | 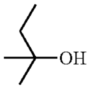 | Vpy/DVB = 98/2 | 1 | Methylene chloride | FIG. 1 | 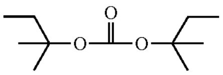 | 71 | A |
| Example 58 | 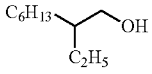 | Vpy/DVB = 75/25 | 1 | Methylene chloride | FIG. 1 | 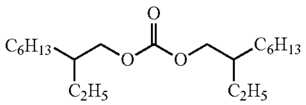 | 74 | A |

Examples 59 to 65

Using the flow type reaction system illustrated in FIG. 1, flow type reactions were carried out in the same manner as in Example 1 by using secondary amines shown in the table below as the active hydrogen-containing compound, where the kinds of solid catalysts with which columns were filled, solvents, and tertiary amines (the matching between numbers and chemical structures of tertiary amines is as described above) were as shown in the table below. The reaction was carried out continuously for 20 hours, during which the purity of the product and the occurrence of temporal clogging were examined. The evaluation standards for clogging were the same as above. The results are shown in the table below.

The abbreviations in the table below are the same as above.

TABLE 5

| | | | | | | Evaluation result | | |
|---|---|---|---|---|---|---|---|---|
| | Secondary amine | Solid catalyst | Tertiary amine | Solvent | Flow type reaction system | Product | Purity (% by mass) | Clogging property |
| Example 59 | 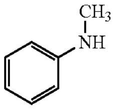 | Vpy/DVB = 98/2 | 1 | Methylene chloride | FIG. 1 | 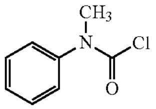 | >97 | A |
| Example 60 | 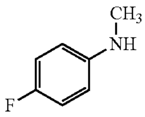 | Vpy/DVB = 98/2 | 1 | Methylene chloride | FIG. 1 | 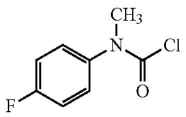 | 88 | A |
| Example 61 | 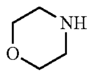 | Vpy/DVB = 98/2 | 1 | Methylene chloride | FIG. 1 | 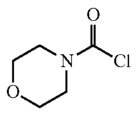 | >97 | A |
| Example 62 | 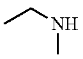 | Vpy/DVB = 98/2 | 1 | Methylene chloride | FIG. 1 | 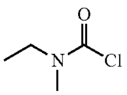 | 93 | B |

TABLE 5-continued

| | Secondary amine | Solid catalyst | Tertiary amine | Solvent | Flow type reaction system | Evaluation result: Product | Evaluation result: Purity (% by mass) | Evaluation result: Clogging property |
|---|---|---|---|---|---|---|---|---|
| Example 63 | 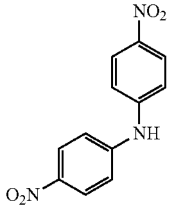 [SMILES: O=[N+]([O-])c1ccc(Nc2ccc([N+](=O)[O-])cc2)cc1] | Vpy/DVB = 98/2 | 1 | Methylene chloride | FIG. 1 | 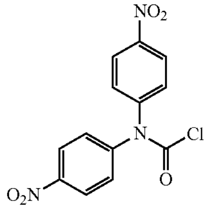 [SMILES: O=C(Cl)N(c1ccc([N+](=O)[O-])cc1)c1ccc([N+](=O)[O-])cc1] | 84 | A |
| Example 64 | 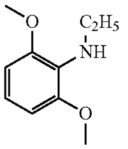 | Vpy/DVB = 98/2 | 1 | Methylene chloride | FIG. 1 | 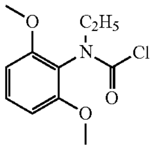 [SMILES: CCN(C(=O)Cl)c1c(OC)cccc1OC] | 89 | A |
| Example 65 | 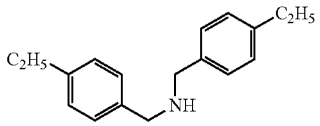 [SMILES: CCc1ccc(CNCc2ccc(CC)cc2)cc1] | Vpy/DVB = 98/2 | 1 | Methylene chloride | FIG. 1 | 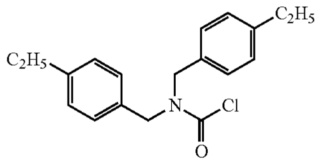 [SMILES: CCc1ccc(CN(Cc2ccc(CC)cc2)C(=O)Cl)cc1] | 83 | A |

Examples 66 to 68

Using the flow type reaction system illustrated in FIG. 1, flow type reactions were carried out in the same manner as in Example 1 by using amino acids as the active hydrogen-containing compound, where the kinds of solid catalysts with which columns were filled, solvents, and tertiary amines (the matching between numbers and chemical structures of tertiary amines is as described above) were as shown in the table below. The reaction was carried out continuously for 20 hours, during which the purity of the product and the occurrence of temporal clogging were examined. The evaluation standards for clogging were the same as above. The results are shown in the table below.

The abbreviations in the table below are the same as above.

TABLE 6

| | Amino acid | Solid catalyst | Tertiary amine | Solvent | Flow type reaction system | Evaluation result: Product | Evaluation result: Purity (% by mass) | Evaluation result: Clogging property |
|---|---|---|---|---|---|---|---|---|
| Example 66 | 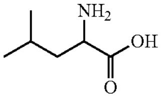 | Vpy/DVB = 98/2 | 1 | Methylene chloride | FIG. 1 | 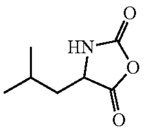 | 95 | A |
| Example 67 | 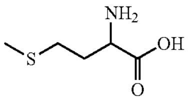 | Vpy/DVB = 98/2 | 1 | Methylene chloride | FIG. 1 | 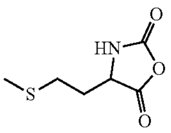 | 94 | A |
| Example 68 | 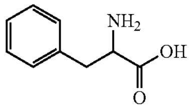 [SMILES: NC(Cc1ccccc1)C(=O)O] | Vpy/DVB = 98/2 | 1 | Toluene | FIG. 1 | 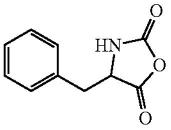 [SMILES: O=C1NC(Cc2ccccc2)C(=O)O1] | 89 | A |

The present invention has been described together with the embodiments of the present invention. However, the inventors of the present invention do not intend to limit the present invention in any part of the details of the description unless otherwise specified, and it is considered that the present invention should be broadly construed without departing from the spirit and scope of the invention shown in the attached "WHAT IS CLAIMED IS".

EXPLANATION OF REFERENCES

100, 200, 300, 400, 500: flow type reaction system iA: triphosgene solution introduction port iB: active hydrogen-containing compound solution introduction port C: tertiary amine solution introduction port I: flow channel having introduction port iA II: flow channel having introduction port iB III: flow channel having introduction port iC IV: reaction flow channel (flow channel for carrying out reaction of introducing a carbonyl group into reaction substrate)

C1: column filled with solid catalyst

M1, M2; joining part

D1: column filled with dehydrating agent

What is claimed is:

1. A method of producing a carbonyl compound by a flow type reaction, comprising:

introducing a triphosgene solution into a flow channel (I), bringing the triphosgene solution into contact with a solid catalyst immobilized in at least a part of the flow channel (I) to generate a phosgene solution while the triphosgene solution is flowing through the flow channel (I), subsequently joining the phosgene solution and an active hydrogen-containing compound solution that flows inside a flow channel (II) at a joining part to form a joining solution, then sending the joining solution downstream inside a reaction flow channel, and reacting the phosgene solution and the active hydrogen-containing compound in the presence of a tertiary amine solution distinct from the solid catalyst, wherein the tertiary amine solution that flows inside a flow channel (III) is introduced downstream of the solid catalyst or at the joining part in the reaction flow channel, and obtaining a carbonyl compound in the joining solution, wherein a tertiary amine of the tertiary amine solution has a cyclic structure, wherein an equivalent diameter of the flow channel (I) is from 0.2 to 50 mm, wherein an equivalent diameter of the flow channel (II) is from 0.1 to 50 mm, wherein the bringing of the triphosgene solution into contact with the solid catalyst immobilized in the flow channel (I) is carried out in an absence of the tertiary amine solution introduced downstream of the solid catalyst or at the joining part where the phosgene solution and the active hydrogen-containing compound solution meet, the solid catalyst is a conversion catalyst that acts on triphosgene to generate phosgene, the solid catalyst is insoluble in a solvent in the triphosgene solution and the solid catalyst is a polymer, the tertiary amine solution acts as a neutralizing agent for hydrochloric acid generated during the reaction, and wherein a pressure after 20 hours passed at the time when a liquid feeding becomes stable and the reaction is in a steady state inside the flow channel (III) is less than 0.1 MPa.

2. The method of producing a carbonyl compound according to claim 1, wherein a temperature in the reaction flow channel is set to be lower than a boiling point of a solvent of which the boiling point is lowest among solvents that are used in the reaction.

3. The method of producing a carbonyl compound according to claim 1, wherein a column filled with the solid catalyst is incorporated in the flow channel (I) to immobilize the solid catalyst in the flow channel (I).

4. The method of producing a carbonyl compound according to claim 1, wherein the polymer has a heteroatom.

5. The method of producing a carbonyl compound according to claim 1, wherein the tertiary amine of the tertiary amine solution has 6 to 40 carbon atoms.

6. The method of producing a carbonyl compound according to claim 1, wherein the active hydrogen-containing compound is at least one of a primary amine, a secondary amine, an alcohol, a thiol, a carboxylic acid, or an amino acid.

7. The method of producing a carbonyl compound according to claim 1, wherein the active hydrogen-containing compound is a primary amine.

8. The method of producing a carbonyl compound according to claim 1, wherein the method further comprises a dehydrating agent arranged in at least one of the flow channel (I) and the flow channel (II).

9. The method of producing a carbonyl compound according to claim 1, wherein the solid catalyst is an imidazole group-modified polymer or a crosslinked polyvinylpyridine.

10. The method of producing a carbonyl compound according to claim 1, wherein the equivalent diameter of the flow channel (I) is from 0.2 mm to 50 mm to suppress clogging of the flow channel (I) during a continuous operation and suitably to control a liquid temperature.

11. The method of producing a carbonyl compound according to claim 1, wherein the equivalent diameter of the flow channel (II) is from 0.1 mm to 50 mm to suppress clogging of the flow channel (II) during a continuous operation and suitably to control a liquid temperature.

* * * * *